United States Patent
Hall

(10) Patent No.: US 8,657,601 B2
(45) Date of Patent: Feb. 25, 2014

(54) IMPLANT FOR EXAMPLE DENTAL IMPLANT

(75) Inventor: Jan Hall, Gothenburg (SE)

(73) Assignee: Nobel Biocare Services AG, Kloten (CH)

( * ) Notice: Subject to any disclaimer, the term of this patent is extended or adjusted under 35 U.S.C. 154(b) by 39 days.

(21) Appl. No.: 10/482,736

(22) PCT Filed: Jun. 26, 2002

(86) PCT No.: PCT/SE02/01257
§ 371 (c)(1),
(2), (4) Date: Jun. 25, 2004

(87) PCT Pub. No.: WO03/003939
PCT Pub. Date: Jan. 16, 2003

(65) Prior Publication Data
US 2005/0221258 A1    Oct. 6, 2005

(30) Foreign Application Priority Data
Jul. 4, 2001   (SE) ....................... 0102391

(51) Int. Cl.
*A61L 27/54* (2006.01)

(52) U.S. Cl.
USPC ............ 433/173; 623/23.55; 623/23.76

(58) Field of Classification Search
USPC ............ 433/173; 623/23.5, 23.55, 23.76
See application file for complete search history.

(56) References Cited

U.S. PATENT DOCUMENTS

| | | | | |
|---|---|---|---|---|
| 4,615,678 A * | 10/1986 | Moermann et al. | ........ | 433/201.1 |
| 5,458,653 A * | 10/1995 | Davidson | .................. | 623/23.36 |
| 5,478,237 A * | 12/1995 | Ishizawa | .................... | 433/201.1 |
| 5,584,693 A * | 12/1996 | Nishihara | ...................... | 433/169 |
| 5,642,996 A * | 7/1997 | Mochida et al. | .............. | 433/174 |
| 5,759,033 A * | 6/1998 | Elia | ................ | 433/173 |
| 5,766,009 A * | 6/1998 | Jeffcoat | ........................ | 433/173 |
| 5,772,439 A * | 6/1998 | Yamaoka et al. | .......... | 433/201.1 |
| 5,876,446 A * | 3/1999 | Agrawal et al. | ............ | 623/23.61 |
| 5,888,067 A * | 3/1999 | Gibbs et al. | .................... | 433/173 |
| 6,068,479 A * | 5/2000 | Kwan | ........................ | 433/173 |
| 6,136,369 A * | 10/2000 | Leitao et al. | ................. | 427/2.27 |
| 6,227,857 B1 * | 5/2001 | Morgan et al. | ................ | 433/173 |
| 6,261,586 B1 * | 7/2001 | McKay | ........................ | 424/423 |
| 6,312,472 B1 * | 11/2001 | Hall et al. | .................. | 623/23.53 |
| 6,419,708 B1 * | 7/2002 | Hall et al. | .................. | 623/23.57 |
| 6,461,385 B1 * | 10/2002 | Gayer et al. | ............... | 623/23.51 |
| 6,730,129 B1 * | 5/2004 | Hall | .......................... | 623/23.57 |

(Continued)

FOREIGN PATENT DOCUMENTS

| | | | |
|---|---|---|---|
| WO | WO-96/16811 A1 | 8/1996 | |
| WO | WO-00/72776 A1 | 12/2000 | |
| WO | WO-00/72777 A1 | 12/2000 | |

*Primary Examiner* — Ralph Lewis
(74) *Attorney, Agent, or Firm* — Walter Ottesen P.A.

(57) ABSTRACT

An implant (10) has one or more surfaces (10a, 10b) with a basic or starting surface structure (1a) derived from mechanical working. A topographic modification of the surface structures is arranged on said surface structure or surface structures. The topographic modification can be formed, for example, by means of shot-peening, etching, plasma spraying, chemical action, etc. The topographically modified surface structures support bone-growth-stimulating agent. In a method for producing the implant, three subsidiary methods are used for carrying out the mechanical working, the topographical modification, and the application of the bone-growth-stimulating agent. An important niche in the demand which exists in the field of implants is thus covered in an advantageous manner.

36 Claims, 2 Drawing Sheets

(56) References Cited

U.S. PATENT DOCUMENTS

| | | | |
|---|---|---|---|
| 6,918,766 B1 * | 7/2005 | Hall et al. | 433/201.1 |
| 7,048,541 B2 * | 5/2006 | Hall et al. | 433/201.1 |
| 7,281,925 B2 * | 10/2007 | Hall | 433/174 |
| 2001/0053937 A1 * | 12/2001 | Johnson et al. | 623/23.34 |

* cited by examiner

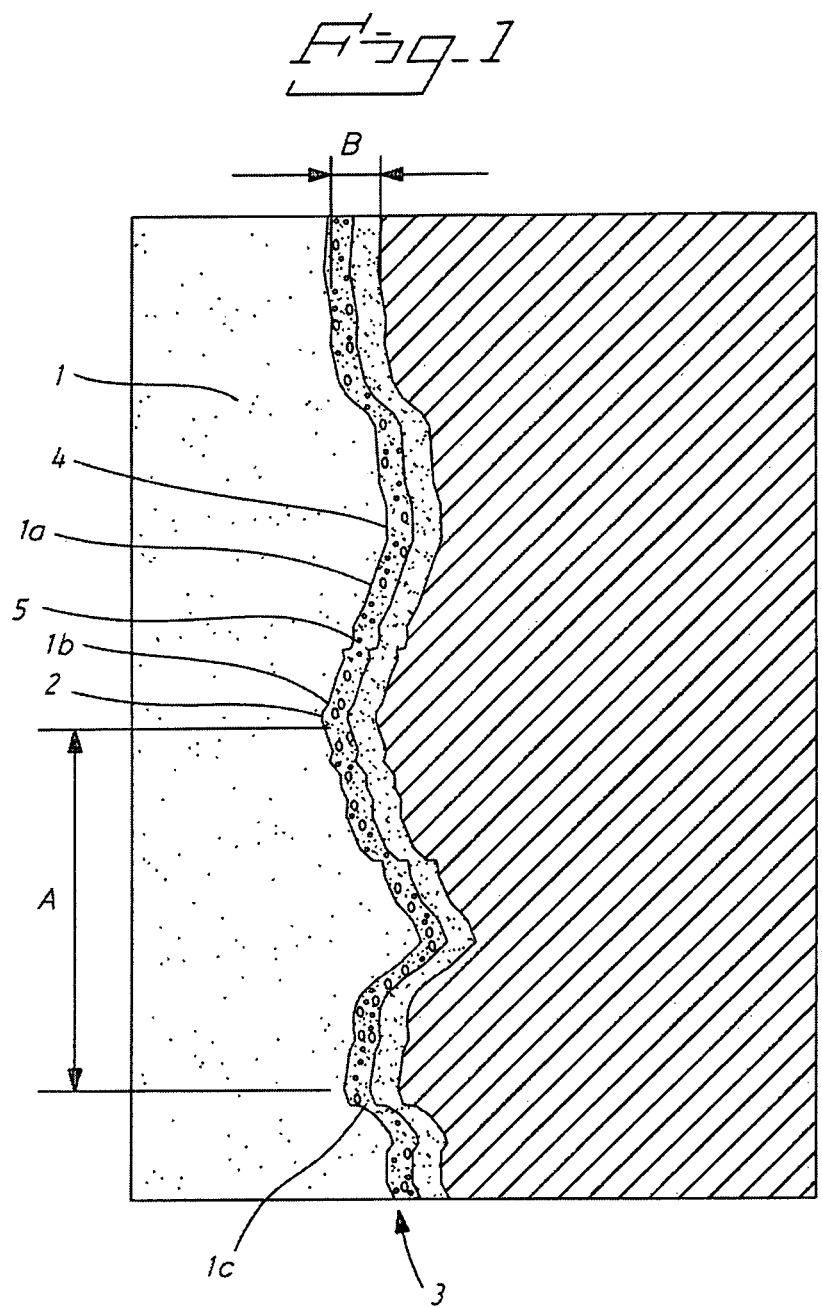

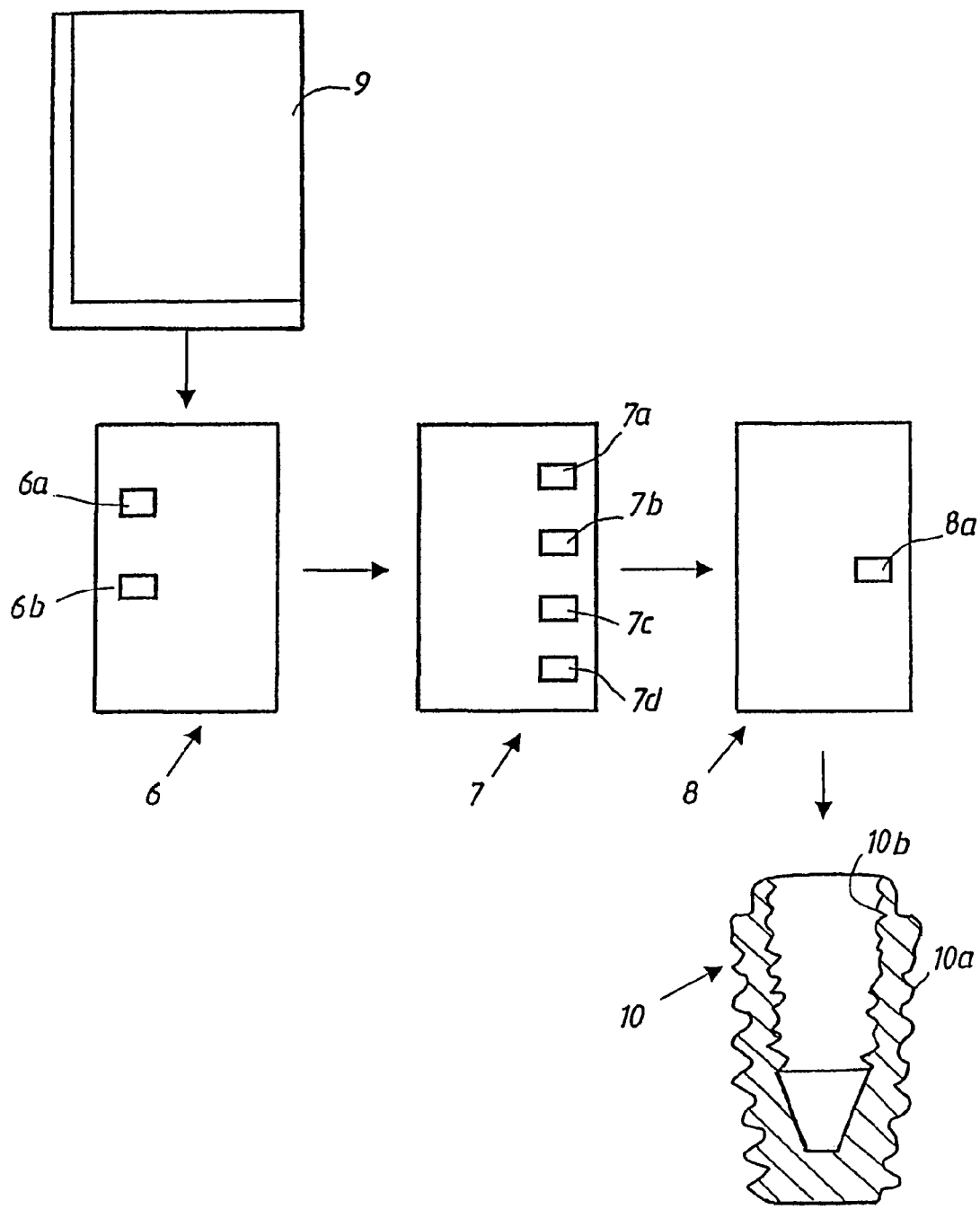

IMPLANT FOR EXAMPLE DENTAL IMPLANT

The present invention relates to an implant or a fixture, for example a dental implant or a dental fixture. The invention also relates to a method for producing the implant or the fixture.

A large number of implants (fixtures) and of methods for producing the implants and applying them in a bone, for example the jaw bone, are already known. It is thus known to give the implant or the fixture different types of surface structures by means of which the implant is intended to cooperate with the bone structure in question. Different types and methods for producing mechanically worked surfaces with the aid of milling, turning, etc., have been proposed in this connection. The surfaces produced have in known cases been further treated with surface-treating devices, for example polishing devices. It is also already known to configure the surfaces with more or less porous oxide layers (titanium oxide layers). It is also already known per se to propose using different types of bone-growth-stimulating or bone-growth-maintaining agents. Different types of bone-growth-stimulating agents can be present in this connection, an example which may be mentioned being the various types of BMP (bone morphogenetic proteins).

Reference is made, inter alia, to the patent applications filed by the same Applicant as in the present patent application, namely WO 98/48862, 9901971-3, 9901974-7, 0001201-3 and 0001202-1. Reference is also made to the prior art cited in said patent applications.

Reference is also made to "Applied Osseointegration Research", pages 5-8 inter alia, published by the "Department of Biomaterials/Handicap Research", Gothenburg (Sweden), October 2000.

In different implant contexts, there are a great many implant situations in which account must be taken of bone status, the status of the patient in other respects, the technical and cost aspects, access to assistance, locality of the patients and of the treatment and production units, etc. There is therefore a need to achieve a very high degree of adaptation of the technical requirements and the implant structures to the different individuals and their situations. The present invention aims to solve this problem by covering an important niche in the treatment range and building, among other things, on the recognition that it is essential to be able to increase the surface areas between the implant and the bone tissue which surrounds the implant, and to modify the original bone wall against the implant with the aid of bone-growth-stimulating agent which stimulates bone sealing. The inventor has recognized the importance of combining the bone-growth-stimulating functions in question with mechanical surfaces which give surface-specific properties so that the implant has the best possible stability and load-bearing capacity in bone which from the start can be attributed to the category of suboptimal bone. A predominant problem to be solved in this context is that the loading capacity must be increased at the interface or transition between the implant and the original bone structure. The geometry of the implant is of fundamental importance for effective load distribution, and the surfaces and topography of the implant play an important role here. It is therefore not sufficient in itself to propose or use a topographical adjustment, nor is it sufficient to propose a purely general use of tissue modification by means of bone-growth-stimulating agent. Also, porous oxide layers which give very good results in some cases cannot be used in other cases.

That which can mainly be regarded as characterizing the novel implant or the novel fixture is that, on one or more surfaces, preferably outwardly directed surfaces, the implant or fixture has an underlying basic or starting structure derived from mechanical working which can include milling, turning, etc. Further characteristics are that, on said basic or starting surface structure or surface structures, the implant has a topographic modification of the basic or starting structure, which topographic modification consists of a surface structure or surface structures formed by shot-peening, etching, chemical action (also wet chemistry) and/or laser, and that the topographically modified surface structure or surface structures support(s) bone-growth-stimulating and/or bone-growth-maintaining agent, which in one illustrative embodiment can be BMP.

In further embodiments of the inventive concept, the topographically modified surface or surfaces is (are) adapted to the bone structure in question in order to afford excellent stability and a load-distributing effect in the transition zone between the implant and the bone structure. The quantity of bone-growth-stimulating and/or bone-growth-maintaining substance or agent causes a modification of the tissue (which can be jaw-bone tissue) surrounding the implant adapted to the topographically modified surface structure or surface structures. Moreover, in said embodiments, the topographically modified surface or surfaces can be intended to bring about a good retention function for the growth-stimulating and/or growth-maintaining substance. The topographically modified surface structure or surface structures is (are) made up of layers which lack any substantial porosity, and, finally, the bone-growth-stimulating and/or bone-growth-maintaining agent or agents or substance or substances on the topographically modified surface structure or surface structures form(s) one or more layers or one or more coatings of dried-in agent.

A method according to the invention can mainly be regarded as being characterized by three different subsidiary methods where, in the first subsidiary method, the dental implant is produced from a blank, preferably of titanium, which is manually worked to produce one or more basic or starting surface structures; in a second subsidiary method, the implant with the basic or starting structure(s) thus given to it is worked with means or processes which topographically modify the structure or structures in order to obtain one or more topographically modified or surface-specific surfaces; and, in a third subsidiary method, the topographically modified or surface-specific surface or surfaces is (are) coated with bone-growth-stimulating and/or bone-growth-maintaining agent or substance, which in this case can be, for example, of the BMP type.

In further embodiments of the inventive concept, the method is characterized by the fact that the agent which is dried onto the surfaces forms one or more dried-in layers, and/or that the quantity of bone-growth-stimulating and/or bone-growth-maintaining agent is chosen as a function of the existing bone quality. In a further embodiment of the method, the topographically modified surface structure or surface structures is (are) chosen for optimum stability and load-distributing effect in the bone structure in question.

By means of what has been proposed above, a solution has been afforded to cover an important niche in the treatment range, it being possible at the same time to use means and subsidiary methods known per se. The combination of measures and structuring proposed according to the present invention is not previously known, even though the different subsidiary methods and structures may be known per se. This paves the way for the novel implant to be used in existing channels of production, distribution and sale, without changes having to be made. The subject of the invention is also compatible with prevailing research in the field and follows or is in line with the verifications gradually being made in the field.

A presently proposed embodiment of an implant or a fixture and a method for producing the implant or the fixture will be described below with reference to the attached drawings, in which:

FIG. 1 shows, in vertical section and at a scale of 10 µm, parts of an implant (fixture) for application in a recess in a bone, for example the jaw bone, and FIG. 2 shows, in block diagram form, a method for producing an implant (fixture) in three different subsidiary methods.

In FIG. 1, parts of an implant are indicated by 1. The implant parts in question are in the present case the outer parts of an implant. The outer parts can be applied on the outer thread of an implant or on another part of the implant. The implant is intended to be applied in bone, which in the present case is preferably the jaw bone, which is provided with a hole or a recess. The implant is screwed into the bone, in a manner already known per se, via an outer thread. The implant and the bone are shown at a scale of ca. 10 µm. In accordance with the concept of the invention, the implant is produced by means of mechanical working, which can include milling, turning, etc. The working in question gives a basic or starting structure which is shown by 1a.

In accordance with the concept of the invention, said basic or starting structure 1a is to be topographically modified. The topographic modification can be obtained by etching, shot-peening, plasma spraying and/or electrochemical treatment (e.g. anodic oxidation), wet chemistry, laser, etc.

In the present case, the topographic modification has been obtained by means of etching and anodic oxidation. The etching gives the basic structure a certain roughness, symbolized by pits 2, 3, where a distance A between the deepest parts 1b and 1c of the pits is of the order of 10-20 µm. Said distance A is to be regarded as an average distance between the pits for the surface or the structure 1a in its entirety. The depth of the pits has been indicated by B in FIG. 1, the minimum depth being of the order of 1 µm. The roughness Ra can assume values of between 0.5 and 2.5 µm (depending on which method is used to measure the roughness). The anodic oxidation gives the surface a porous oxide layer, symbolized by 4 in the figure.

Likewise in accordance with the concept of the invention, the surface which has been topographically modified in this way is coated with bone-growth-stimulating agent, symbolized by 5 in the figure, bone-growth-stimulating agent here being understood in its most general sense. In a preferred embodiment, bone-growth-stimulating agent in the form of rhBMP is used. In preferred embodiments, use is made of rhBMP-2, rhBMP-4, rhBMP-7, etc. A characteristic of the surface structure, the modification and the layer of bone-growth-stimulating agent is that the latter has a high degree of retention.

FIG. 2 shows how an implant according to the present disclosure can be produced with the basic structure described, the topographic modification and the application of bone-growth-stimulating agent in three different subsidiary methods which are indicated by, 7 and 8. In FIG. 2, a starting blank of titanium or of another tissue-compatible material is indicated by 9. The blank is brought to a device which executes the first subsidiary method which involves the formation of the implant's structure and mechanical working of one or more outer surfaces and/or one or more inner surfaces. The mechanical treatment and working of the blank can be carried out, for example, by means of turning in a lathe 6a. As an alternative or as a complement to this, the outer and inner contour in question can be produced by milling in a milling device 6b. Reference is made here to the prior art. After the first subsidiary method has been completed, the product (implant) produced in the first subsidiary method is transferred to a device which is used in the second subsidiary method for topographic modification of the surface structures which have been turned or milled in the first subsidiary method. The modification means in question can operate with etching, the etching apparatus having been indicated by 7a. Alternatively, the surface can be topographically modified by means of shot-peening, the device for this having been indicated by 7b. As a third alternative, the modification can be carried out by plasma spraying or electrochemical treatment, the devices for this having been indicated by 7c and 7d, respectively. One or more of said modification principles can be used. One example of electrochemical treatment which may be mentioned is anodic oxidation. The topographically modified product (the implant) is then transferred to the device carrying out the third subsidiary method, said device having been indicated y 8a in FIG. 2. Bone-growth-stimulating agent can be applied, for example, by means of immersion or plasma spraying, etc. In the case of application by immersion in liquid which has been provided with hone-growth-stimulating agent, the topographically modified implant is immersed in the liquid for about half an hour and then subjected to drying, for example for 6 hours.

After the treatment in the third subsidiary stage, a finished implant 10 is thus obtained. In the present case, the implant comprises one or more outer threads 10a and also one or more inner threads 10b. The threads can be provided with surface structures of different or identical sizes, and the topography can thus be different along the extent of the surface structure in the longitudinal direction of the implant. The finished implant can be made ready for supply to the dentist or surgeon in question. Alternatively, parts of the production, for example parts which carry out the third subsidiary method, can be supplied to the dentist together with the semi-finished implant produced in the first and second subsidiary methods. Bone-growth-stimulating agent can be applied to the modified surface structure in a manner known per se, in which connection reference may be made inter alia to the Swedish patent applications filed by the same Applicant on the same day: SE 9901971, SE 9901972, and SE 9901973, which are counterpart applications of U.S. Pat. Nos. 7,708,558, 6,918, 766, and 6,730,129, respectively. The quantity of bone-growth-stimulating and/or bone-growth-maintaining agent is chosen to optimally connect to the topographically modified surface structure or surface structures. In accordance with the prior art, optimum bone growth is to be created in the tissue surrounding the implant, i.e. the bone tissue. An important feature of the invention is that the different subsidiary methods permit application of bone-growth-stimulating agent in one or more layers with good retention, which means that the agent can move gradually and in a controlled manner over to the bone tissue which surrounds the implant.

The invention is not limited to the embodiment shown above by way of example, and instead it can be modified within the scope of the attached patent claims and the inventive concept.

The invention claimed is:
1. An implant for application in bone, which comprises:
  a) at least one surface, having an underlying basic or starting structure derived from mechanical working,
  b) having a topographic modification on said basic or starting surface structure, which topographic modification gives a surface structure or surface structures formed by shot-peening, etching, plasma spraying and/or chemical action, and c) rhBMP bone-growth-stimulating and/or rhBMP bone-growth-maintaining agent supported by the topographically modified surface structure, wherein said rhBMP bone-growth-stimulating and/or rhBMP bone-growth-maintaining agent is selected from the group consisting of rhBMP-2, rhBMP-4 and rhBMP-7, wherein the modified surface structure has pits wherein the average distance between the deepest parts of the pits is about 10-20 μm and the minimum depth of the pits is about 1 μm, and wherein said surface structure is formed by anodic oxidation and the modified surface structure comprises a porous oxide layer.

2. The implant as claimed in claim 1, intended to be applied in a hole or recess in a bone, wherein the topographically modified surface affords excellent stability and a load-distributing effect in the transition zone between the implant and the bone structure to which it is to be applied.

3. The implant as claimed in claim 2, wherein the quantity of bone-growth-stimulating and/or bone-growth-maintaining agent is sufficient to cause a modification of tissue of the bone to which the implant is to be applied.

4. The implant as claimed in claim 2, wherein the topographically modified surface is intended to bring about a good retention function for the bone-growth-stimulating and/or bone-growth-maintaining agent.

5. The implant as claimed in claim 2, wherein the bone-growth-stimulating and/or bone-growth-maintaining agent on surface structure form one or more layers of dried-in agent or substance.

6. The implant as claimed in claim 1, wherein the quantity of bone-growth-stimulating and/or bone-growth-maintaining agent is sufficient to cause a modification of tissue of the bone to which the implant is to be applied.

7. The implant as claimed in claim 6, wherein the topographically modified surface is intended to bring about a good retention function for the bone-growth-stimulating and/or bone-growth-maintaining agent.

8. The implant as claimed in claim 6, wherein the bone-growth-stimulating and/or bone-growth-maintaining agent on surface structure form one or more layers of dried-in agent or substance.

9. The implant as claimed in claim 1, wherein the topographically modified surface is intended to bring about a good retention function for the bone-growth-stimulating and/or bone-growth-maintaining agent.

10. The implant as claimed in claim 9, wherein the bone-growth stimulating and/or bone-growth-maintaining agent on surface structure form one or more layers of dried-in agent or substance.

11. The implant as claimed in claim 1, wherein the surface structure consists of the porous oxide layer.

12. The implant of claim 11, wherein the bone-growth-stimulating and/or bone-growth-maintaining agent on surface structure form one or more layers of dried-in agent or substance.

13. The implant of claim 1, wherein the bone-growth-stimulating and/or bone-growth-maintaining agent or agents on surface structure form one or more layers of dried-in agent or substance.

14. The implant of claim 1 being a dental implant comprising titanium.

15. The implant of claim 1 being a dental implant and said mechanical working is selected from the group consisting of milling and turning.

16. The implant of claim 1 wherein said at least one surface comprises outwardly directed surfaces.

17. The implant of claim 1 wherein said rhBMP bone-growth-stimulating and/or rhBMP bone-growth-maintaining agent comprises rhBMP-2.

18. The implant of claim 1 wherein said rhBMP bone-growth-stimulating and/or rhBMP bone-growth-maintaining agent comprises rhBMP-4.

19. The implant of claim 1 wherein said rhBMP bone-growth-stimulating and/or rhBMP bone-growth-maintaining agent comprises rhBMP-7.

20. The implant of claim 1 being a dental implant.

21. The implant of claim 1 wherein said surface structure is formed by etching and anodic oxidation.

22. The implant of claim 21 wherein the modified surface structure has a roughness Ra of between 0.5 μm and 2.5 μm.

23. The implant of claim 1, wherein said rhBMP bone-growth-stimulating and/or rhBMP bone-growth-maintaining agent is present in an amount to optimally connect to the topographically modified surface structure.

24. A method for producing one or more surface on an implant for application in bone, comprising the following combination:

a) in a first subsidiary method, the implant is produced from a blank, which is manually worked to produce at least one basic or starting surface structure, b) in a second subsidiary method, the implant with the basic or starting structure thus given to it is worked with means or processes which topographically modify the basic or starting surface structure or surface structures in order to obtain one or more topographically modified or surface-specific surfaces, which modifying means or process is selected from the group consisting of shot-peening, etching, plasma spraying, chemical working, anodic oxidation, and laser working, wherein the modified structure has pits wherein the average distance between the deepest parts of the pits is about 10-20 μm and the minimum depth of the pits is about 1 μm, and c) in a third subsidiary method, the topographically modified or surface-specific surface is coated with rhBMP bone-growth-stimulating and/or rhBMP bone-growth-maintaining agent, wherein said rhBMP bone-growth-stimulating and/or rhBMP bone-growth-maintaining agent is selected from the group consisting of rhBMP-2, rhBMP-4 and rhBMP-7, wherein said modifying means or process comprises anodic oxidation and the modified surface structure comprises a porous oxide layer.

25. The method as claimed in claim 24, wherein the topographically modified or surface-specific surface is coated with bone-growth-stimulating and/or bone-growth-maintaining agent or substance which is dried onto the surface and forms one or more dried-in layers.

26. The method as claimed in claim 24, wherein the quantity of bone-growth-stimulating and/or bone-growth maintaining agent is chosen as a function of the existing bone quality of the bone in which the implant is to be applied.

27. The method as claimed in claim 24, characterized in that the topographically modified surface structure or surface structures are chosen for optimum stability and load-distributing effect in the bone structure in which the implant is to be applied.

28. The method of claim 24 wherein said implant is a dental implant and said blank comprises titanium.

29. The method of claim 24 wherein said implant is a dental implant and said blank is manually worked by a process selected from the group consisting of milling and turning.

30. The method of claim 24 wherein said rhBMP bone-growth-stimulating and/or rhBMP bone-growth-maintaining agent comprises rhBMP-2.

31. The method of claim 24 wherein said rhBMP bone-growth-stimulating and/or rhBMP bone-growth-maintaining agent comprises rhBMP-4.

32. The method of claim 24 wherein said rhBMP bone-growth-stimulating and/or rhBMP bone-growth-maintaining agent comprises rhBMP-7.

33. The method of claim 24 wherein said modifying means or process comprises etching and anodic oxidation.

34. The method of claim 33 wherein the modified surface structure has a roughness Ra of between 0.5 μm and 2.5 μm.

35. The method of claim 24, which further comprises choosing a quantity of said rhBMP bone-growth-stimulating and/or rhBMP bone-growth-maintaining agent to optimally connect to the topographically modified surface structure.

36. An implant for application in bone, which comprises:
a) a titanium blank having at least one surface,
b) a titanium surface structure derived from mechanical working provided on the at least one surface,
c) a topographically modified surface structure provided on the titanium surface structure, and
d) an rhBMP bone-growth-stimulating and/or rhBMP bone-growth-maintaining agent supported by the topographically modified surface structure,
wherein the titanium surface structure has a surface roughness of from 0.5 μm to 2.5 μm,
wherein the topographically modified surface structure is a porous oxide layer prepared by anodic oxidation of the titanium surface structure, and
wherein the rhBMP bone-growth-stimulating and/or rhBMP bone-growth-maintaining agent is selected from the group consisting of rhBMP-2, rhBMP-4 and rhBMP-7.

* * * * *